(12) United States Patent
Maddison et al.

(10) Patent No.: US 11,455,690 B2
(45) Date of Patent: Sep. 27, 2022

(54) PAYER PROVIDER CONNECT ENGINE

(71) Applicant: VVC HOLDING CORPORATION, Seattle, WA (US)

(72) Inventors: Robert Maddison, South Burlington, VT (US); Eric Rose, Boston, MA (US); Donna Maddox, Ballwin, MO (US); Saana Aldridge, Seattle, WA (US)

(73) Assignee: VVC HOLDING CORPORATION, Seattle, WA (US)

( * ) Notice: Subject to any disclaimer, the term of this patent is extended or adjusted under 35 U.S.C. 154(b) by 267 days.

(21) Appl. No.: 15/195,080

(22) Filed: Jun. 28, 2016

(65) Prior Publication Data
US 2017/0372430 A1    Dec. 28, 2017

(51) Int. Cl.
*G16H 20/00*      (2018.01)
*G06Q 40/08*    (2012.01)
(Continued)

(52) U.S. Cl.
CPC ............. *G06Q 40/08* (2013.01); *G16H 10/40* (2018.01); *G16H 10/60* (2018.01); *G16H 30/20* (2018.01); *G16H 40/20* (2018.01)

(58) Field of Classification Search
CPC ........ G16H 10/60; G16H 10/40; G16H 40/20; G16H 30/20; G06F 19/328; G06F 19/00;
(Continued)

(56) References Cited

U.S. PATENT DOCUMENTS 6,024,699 A * 2/2000 Surwit ............... G06F 19/3418
                                                                    600/300
7,912,733 B2 * 3/2011 Clements ............ G06F 19/322
                                                                    705/2
(Continued)

OTHER PUBLICATIONS

Family Physicians Group Improves Patient Experience through Use of PatientPoint(R) Care Coordination Platform: PatientPoint plays key role in strategic patient engagement initiative, May 31, 2013, PR Newswire. (Year: 2013).*

*Primary Examiner* — John A Pauls
(74) *Attorney, Agent, or Firm* — Hanley, Flight & Zimmerman, LLC (57) ABSTRACT

Systems, methods and computer program products to identify and close gaps in care are provided. Aspects of the present disclosure disclosed and described herein enable a payer may identify gaps in care based on information in the payer database. The payer can send this information to the provider prior to patient scheduling. The scheduling system at the provider can use this information to schedule patients and their medical needs (e.g., medical test, lab tests, imaging tests, etc.) before the next patient appointment. Primary care providers (PCPs) can then be made aware of the gaps in care information, as well as Hierarchical Condition Category (HCC) coding gap information, so they can perform a complete diagnosis using all available clinical data. PCP notes along with the treatment the patient receives can be combined with the RAF (Risk Adjustment Score) shared by the payers to ensure patient is assessed for all relevant (Continued)

conditions during the visit. Payers can then be informed electronically that the gap in care has been closed; the payer can also receive the resultant claims such that correct RAF scores can be computed and HCC coding gaps can be closed.

18 Claims, 8 Drawing Sheets

(51) Int. Cl.
*G16H 10/60* (2018.01)
*G16H 10/40* (2018.01)
*G16H 40/20* (2018.01)
*G16H 30/20* (2018.01)

(58) Field of Classification Search
CPC ........ G06Q 10/10; G06Q 50/24; G06Q 40/80; G06Q 50/22–24; G06Q 40/08
See application file for complete search history.

(56) References Cited

U.S. PATENT DOCUMENTS

| | | | |
|---|---|---|---|
| 2009/0099862 A1* | 4/2009 | Fireman | G06F 19/3418 705/2 |
| 2011/0087500 A1* | 4/2011 | McCallum | G06Q 10/10 705/3 |
| 2012/0035948 A1* | 2/2012 | Borton | G06Q 50/22 705/2 |
| 2013/0151271 A1* | 6/2013 | Toleti | G06Q 50/22 705/2 |
| 2015/0019248 A1* | 1/2015 | Anand | G06F 17/28 705/2 |
| 2015/0039343 A1* | 2/2015 | Cline | G16H 50/30 705/3 |
| 2015/0269334 A1* | 9/2015 | Fendell | G06Q 50/22 705/4 |
| 2015/0347705 A1* | 12/2015 | Simon | G16H 10/60 705/3 |
| 2017/0177810 A1* | 6/2017 | Fulton | G06Q 40/08 |
| 2018/0122499 A1* | 5/2018 | Austin | G06F 17/30371 |

* cited by examiner

PAYER PROVIDER CONNECT ENGINE

FIELD OF DISCLOSURE

The present disclosure relates to providing closure for gaps in care for one or more patients using a payer provider connect framework.

BACKGROUND

The statements in this section merely provide background information related to the disclosure and may not constitute prior art.

Strong growth in Medicare, Medicaid and Commercial plan providers in the United States is forcing health plans to improve quality through effective collaboration with physicians and hospitals. However, clinical data exists in many forms and in many different systems (e.g., EMR systems, lab systems, imaging systems, billing systems and scheduling systems) across a hospital setting and more and more data is being shared among the providers (doctors, hospitals, etc.) and payers. The payer is looking for 1) rapid closure of gaps in care; 2) accurate Risk Adjustment Factor scores calculated from claims diagnosis; 3) timely responses to clinical data requests to help payers comply with Centers for Medicare and Medicaid Services (CMS) regulations; and 4) more consistent, higher quality outcomes. At the same time, providers need 1) timely information on gaps in care; 2) guidance on Hierarchical Condition Category (HCC) coding gaps for managed patients when assessing patients; 3) an electronic means to communicate relevant clinical data to payers; and 4) more transparency on the correct clinical metrics to focus on. Thus, lack of efficient payer provider connectivity in Medicare Advantage (MA) is giving rise to a plethora of problems. For example, 15% of Medicare beneficiaries have a minimum of 6 chronic conditions which account for 41% of the spending. Today, payers rely on antiquated methods to retrieve and share medical records with providers; this results in a significant delay in closing gaps in care. Lack of proper infrastructure and standards to share clinical data has resulted in improper risk adjustment scores for patients and collaboration between payers and providers.

BRIEF SUMMARY

In view of the above, there is a need for systems, methods, and computer program products which can help payers and providers share clinical information in near real time using a payer provider connect framework. The above-mentioned needs are addressed by the subject matter described herein and will be understood in the following specification.

According to one aspect of the present disclosure, a system that allows a payer provider connection component that analyzes medical information from one or more payer systems and one or more provider systems and reconciles gaps in care from each of the one or more payer systems and the one or more provider systems is provided.

According to another aspect of the present disclosure, a method that allows a payer provider connection component that analyzes medical information from one or more payer systems and one or more provider systems and reconciles gaps in care from each of the one or more payer systems and the one or more provider systems is provided.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Aspects disclosed and described herein enable providing payers and providers of healthcare a better way to exchange clinical information to help promote better quality outcomes for the patients they serve.

Government mandated electronic medical systems including healthcare payers and healthcare providers have created a lack of efficient payer provider connectivity that has given rise to inadequate and potentially dangerous gaps in medical care that must be taken into account for patient safety. Today, payers rely on an antiquated systems and methods to retrieve and share medical records with providers; this results in significant delay in closing gaps in care. Lack of proper infrastructure and standards to share clinical data has resulted in improper risk adjustment and collaboration between payers and providers. In addition, quality is the new currency of transaction for healthcare payers.

Given the above, the present application provides a way to connect the payer and provider to close the gaps in care. In one aspect, a payer may identify gaps in care based on information in the payer database. The payer can send this information to the provider prior to patient scheduling. The scheduling system at the provider can use this information to schedule patients and their medical needs (e.g., medical test, lab tests, imaging tests, etc.) before the next patient appointment. Primary care providers (PCPs) can then be made aware of the gaps in care information so they can perform a complete diagnosis using all available clinical data. PCP notes along with the treatment the patient receives can be combined with the RAF (Risk Adjustment Score) shared by the payers to ensure patient is assessed for all relevant conditions during the visit. Payers can then be informed electronically that the gap in care has been closed; the payer can also receive the resultant claims such that correct RAF scores can be computed and HCC coding gaps can be closed.

Other aspects, such as those discussed in the following and others as can be appreciated by one having ordinary skill in the art upon reading the enclosed description, are also possible.

II. Example Operating Environment

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices.

Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Figure 1:
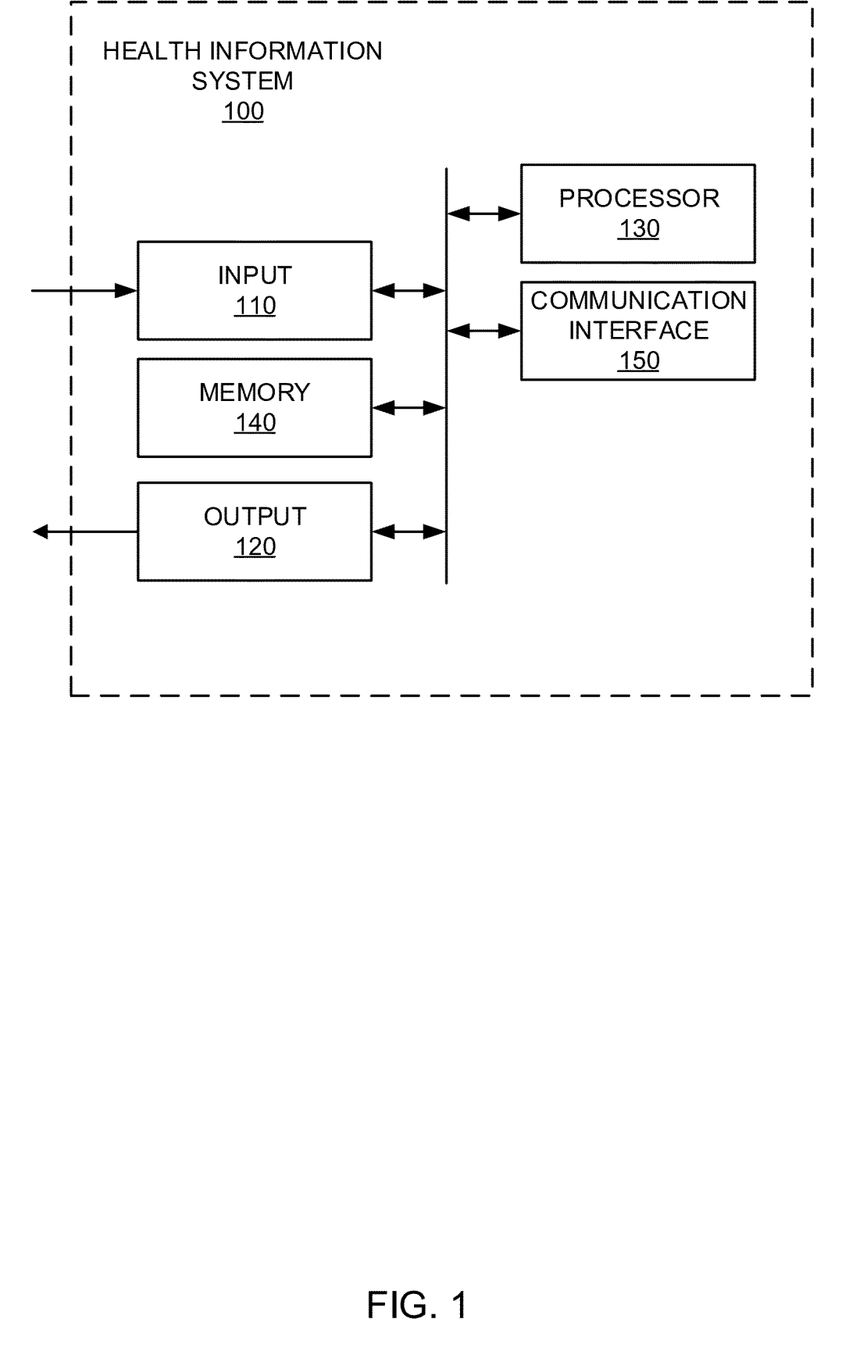
FIG. 1 shows a block diagram of an example healthcare-focused information system.

Turning now to the figures, FIG. 1 shows a block diagram of an example healthcare-focused information system 100. Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touchscreen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
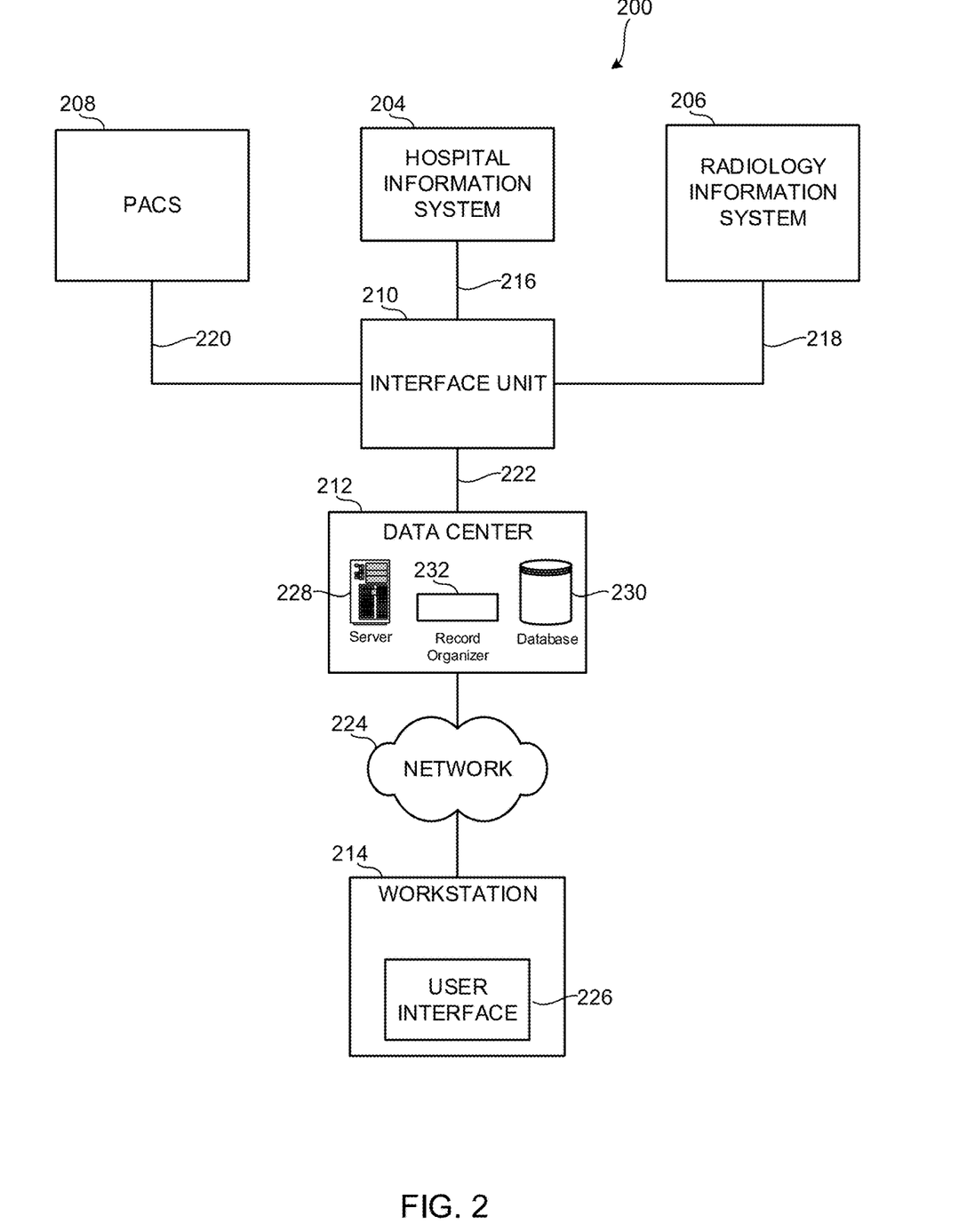
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, RIS 206, and PACS 208 are housed in a healthcare facility and locally archived. However, in other implementations, HIS 204, RIS 206, and/or PACS 208 may be housed within one or more other suitable locations. In certain implementations, one or more of PACS 208, RIS 206, HIS 204, etc., may be implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, RIS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example System

Figure 3:
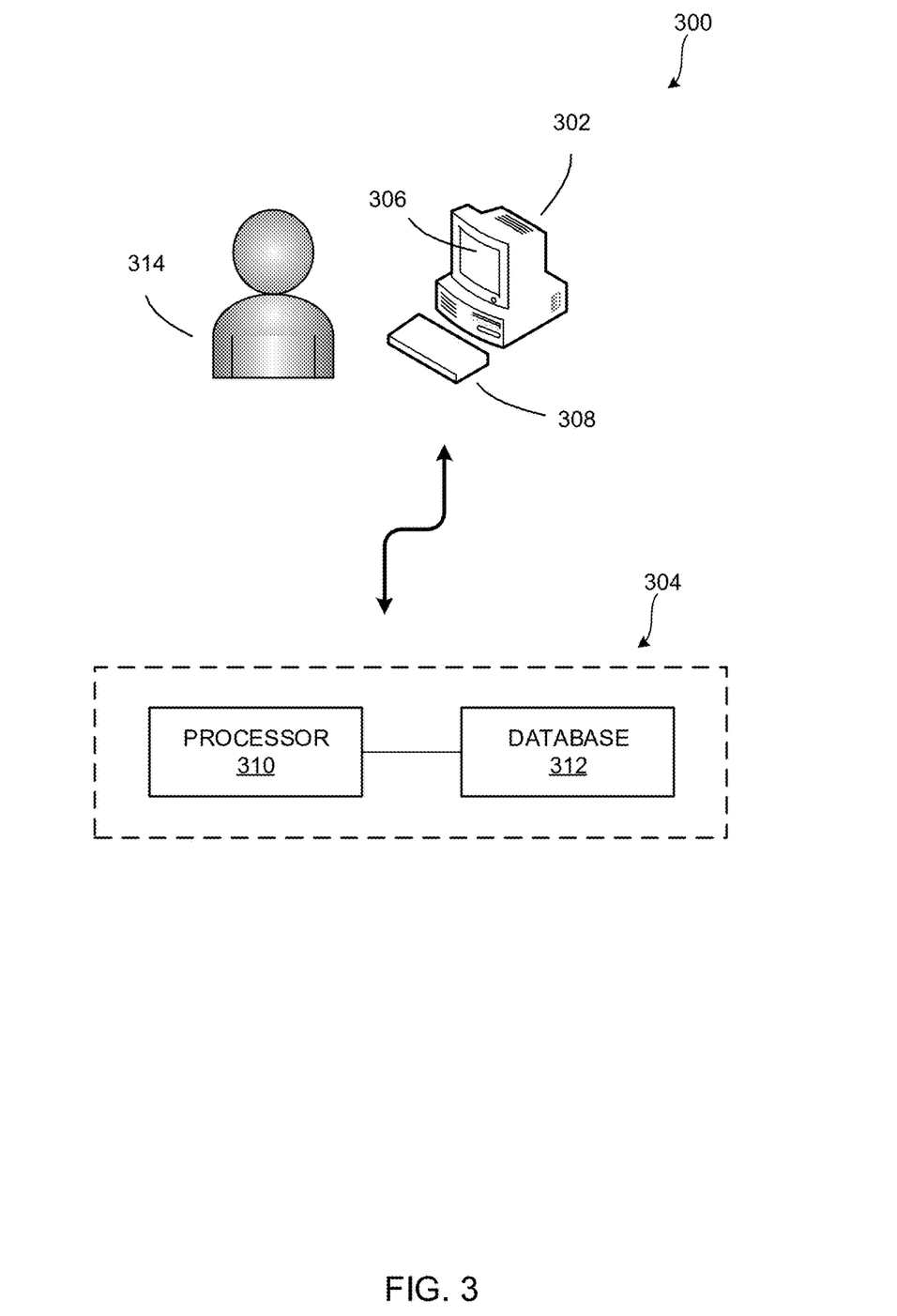
FIG. 3 is a block diagram illustrating an example payer provider connect system, according to the present disclosure.

FIG. 3 depicts an example system 300 for creating payer provider connect capabilities according to one aspect of the present disclosure. System 300 includes a computer 302 and a payer provider connect engine 304 communicatively coupled to computer 302. In this example, computer 302 includes a user interface 306 and a data input (e.g., a keyboard, mouse, microphone, etc.) 308 and payer provider connect engine 304 includes a processor 310 and a database 312.

In certain aspects, user interface 306 displays data such as data and images received from payer provider engine 304. In certain aspects, user interface 306 receives commands and/or input from a user 314 via data input 308. In certain aspects where system 300 is used to provide electronic clinical data exchange, user interface 306 displays a clinical, billing and other healthcare-related data.

Figure 4:
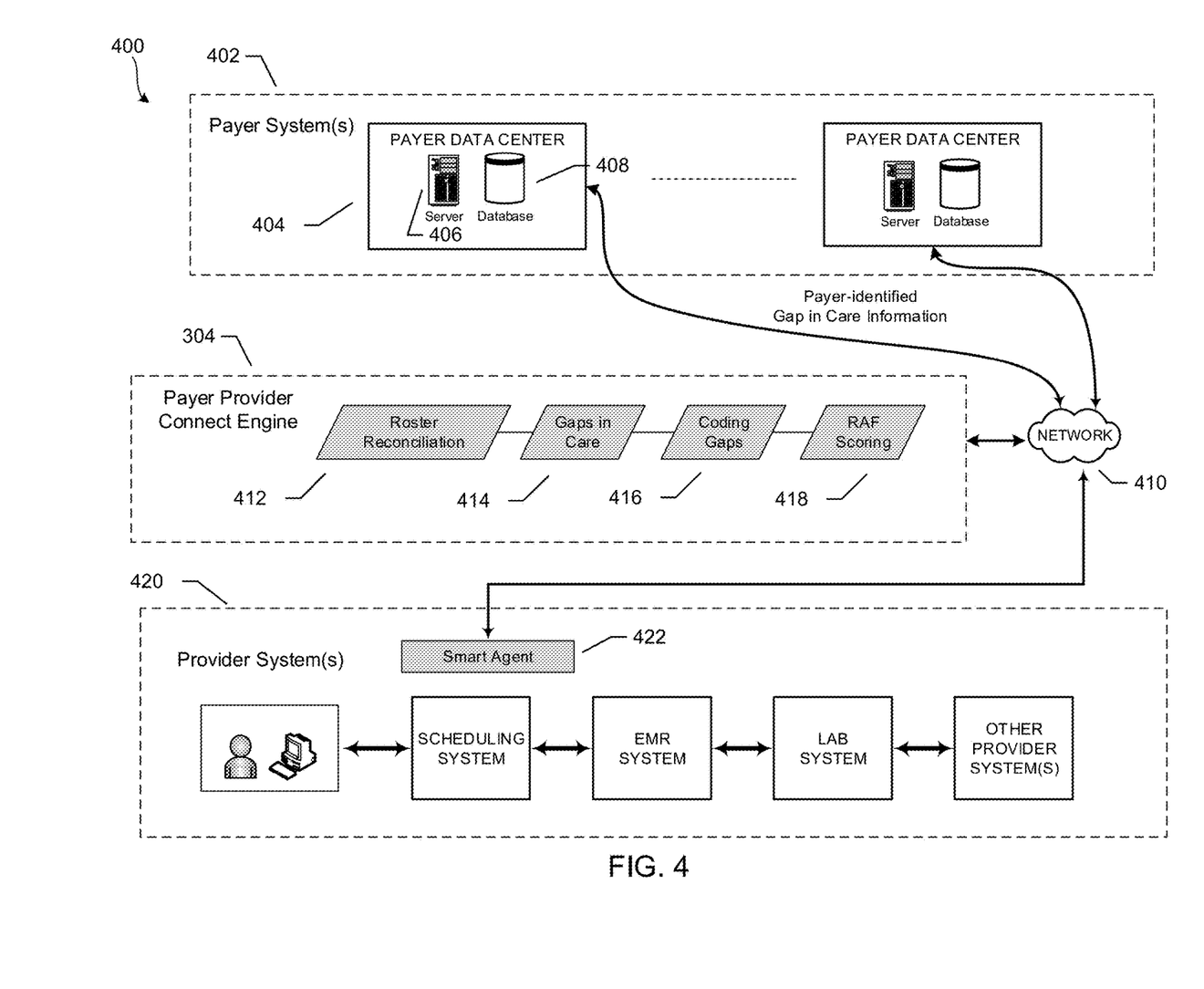
FIG. 4 is a block diagram illustrating an example payer provider connect system and its relationship to other systems, according to the present disclosure.

FIG. 4 illustrates a flow diagram of payer provider connect engine 304 according to one aspect of the present disclosure. In certain aspects, one or more Payer Systems 402 contain payer data centers 404 which comprise servers 406 and databases 408. In certain aspects, one or more Payer Systems 402 identify Gap(s) in Care (GiC). Payer provider connect engine 304 receives payer-identified GiC from one or more Payer Systems 402 via network 410. In certain aspects, Payer provider connect engine 304 performs Roster Reconciliation 412 to match Payer members with Provider patients, consolidation of GiC 414, identifies additions Coding Gaps 416, and/or computes Risk Adjustment Score (RAF Scoring) 418. Payer provider engine simultaneously sends the consolidated information from each of these factors through network 410 to one or more provider systems 420.

In certain aspects, payer provider connect engine 304 is connected to a smart agent 422. In certain aspects, smart agent 422 performs one or more functions. These function can include but are not limited to: 1) Centralized Cloud Management where centralized administration for the deployed smart agents includes monitoring and alerting; 2) Centralized Cloud Deployment where content can be built centrally and can be deployed and updated from the cloud or other servers to deployed smart agents; 3) Secure Bi-directional Data Exchange which supports bi-directional data exchange using configured endpoints and adaptors; 4) Certificate Management which provides the ability to install and manage customer-specific certificates to ensure secure encrypted communication; 5) Endpoint connections which include SFTP, SOAP, web service, REST/JSON services, Disk/File and database connections; 5) Plug-in adapters which provide support for the creation of customized plug-in application specific adaptors; 6) Configurable routes to enable complicated data exchange; and 7) Message Queuing which manages the data load and ensures eventual delivery of all messages.

In certain aspects, provider systems 420 identify GiC and communicate the GiC to the payer provider connect engine 304 and/or directly to payer systems 402 via network 410.

IV. Example Method

Member Roster Management

Figure 5:
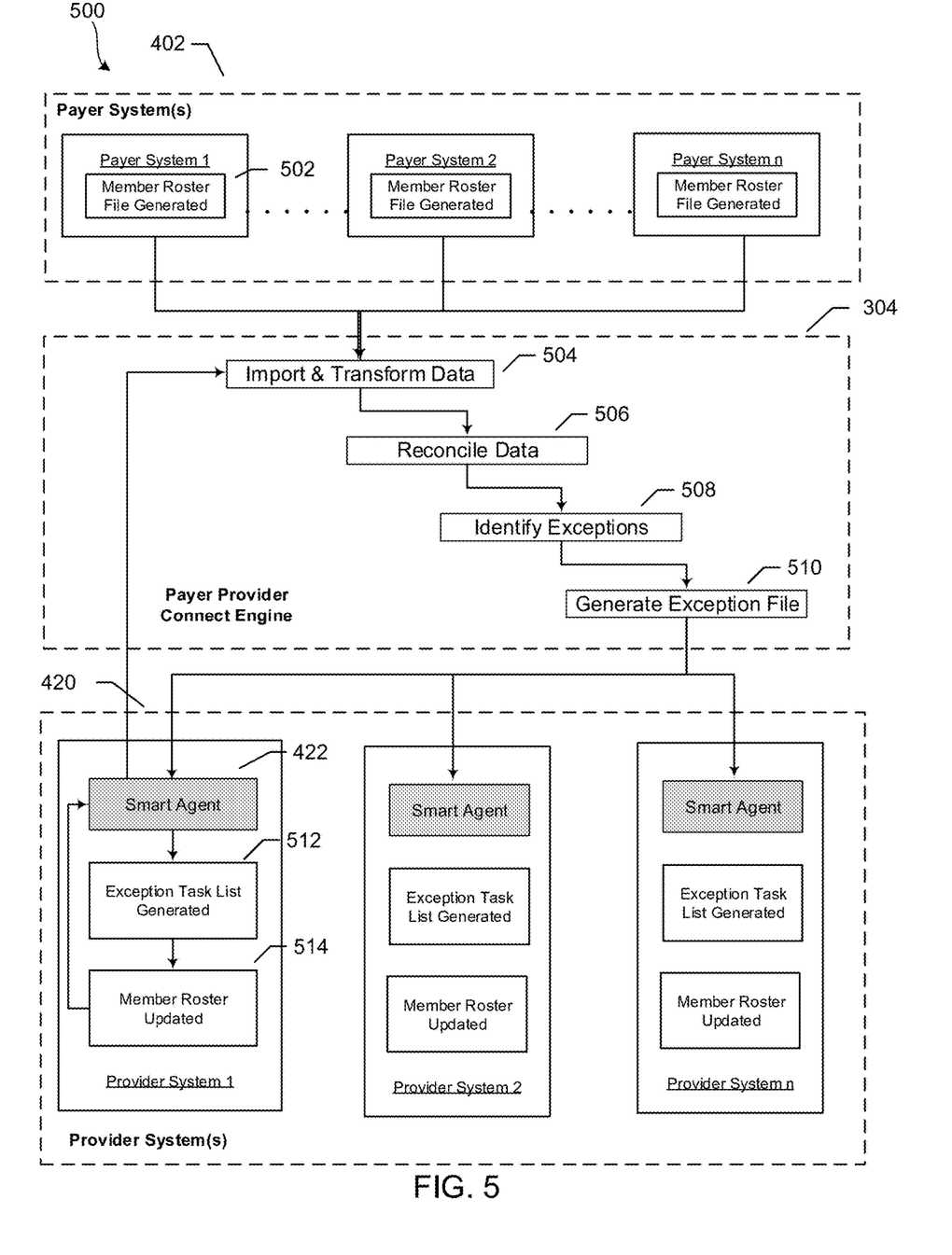
FIG. 5 shows a flow diagram illustrating an example method of operating the system of FIG. 3 for analyzing member rosters, according to the present disclosure.

Referring now to FIG. 5, in certain examples, payer systems 402 generates a member roster file 502 and transmits the data to payer provider connect engine 304. In certain aspects, data may be from multiple provider practices. Payer provider connect engine 304 imports and transforms the data 504 into a common format that payer provider connect engine 304 can understand. Once the data has been transformed the data is reconciled 506 to compile a complete member list from all the different payer systems 402. Member list exceptions are identified 508, between each payer system 402 and each provider system 420 and an exception file 510 is generated and sent to each provider system's 420 smart agent 422. In certain aspects, smart agent 422 unencrypts the file and imports the roster exceptions. Provider systems 420 reads the roster exceptions and generates an exception task list 512 from which member rosters 514 is updated. In certain aspects, administrative staff at the provider can review the tasks and update enrollment information for a patient. In certain aspects, the tasks are updated automatically by payer system 420. Note update file may contain member updates from multiple payers. In certain aspects, the updated member roster 514 is sent to smart agent 422 which transmits the data to payer provider connect engine 304. Payer provider connect engine 304 imports the data 504, reconciles the data 506 and applies the member roster updates across the provider systems as described above.

Hierarchical Condition Category (HCC) Coding Gap

Figure 6:
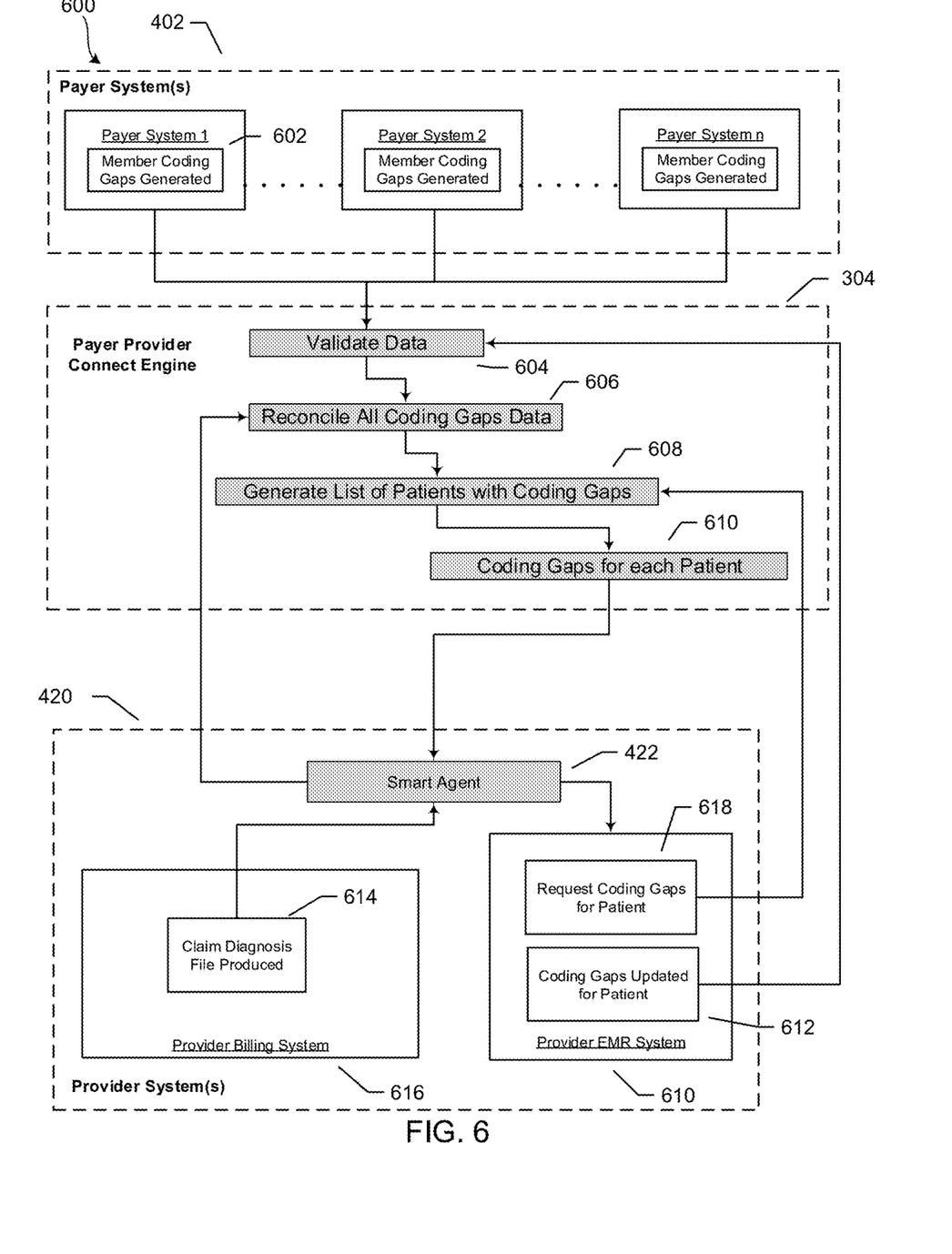
FIG. 6 shows a flow diagram illustrating an example method of operating the system of FIG. 3 for analyzing coding gaps, according to the present disclosure.

Referring now to FIG. 6, in certain examples, payer systems 402 generates member coding gaps 602. In certain aspects member coding gap 602 may contain data from multiple provider practices. Payer system 402 transmits member coding gaps 602 data to payer provider connect engine 304. Payer provider connect engine 304 imports and transforms the data 504 into a common format that payer provider connect engine 304 can understand. Payer provider 304 imports and validates data 604 and then reconciles all coding gaps data 606. In certain aspects, a list of patients with coding gaps 608 is generated. Furthermore, a member coding gap file is generated for each patient 610 and sent to one or more provider systems 420 via smart agent 422. Smart agent 422 sends the coding gaps to provider EMR systems 610. In certain aspects, coding gaps are updated for each patient 612 and sent back to payer provider connect engine 304 to reconcile the updated information and send it out to other provider systems 420.

In certain aspects, claim diagnosis file 614 is produced from provider billing system 616 which send the file to smart agent 422 for transmission back to payer provider connect engine 304 to reconcile the updated information and send it out to other provider systems 420. In certain aspects, provider EMR system 610 can request coding gaps for a patient 618 and send the request to payer provider connect engine 304.

Gap in Care Health Alert

Figure 7:
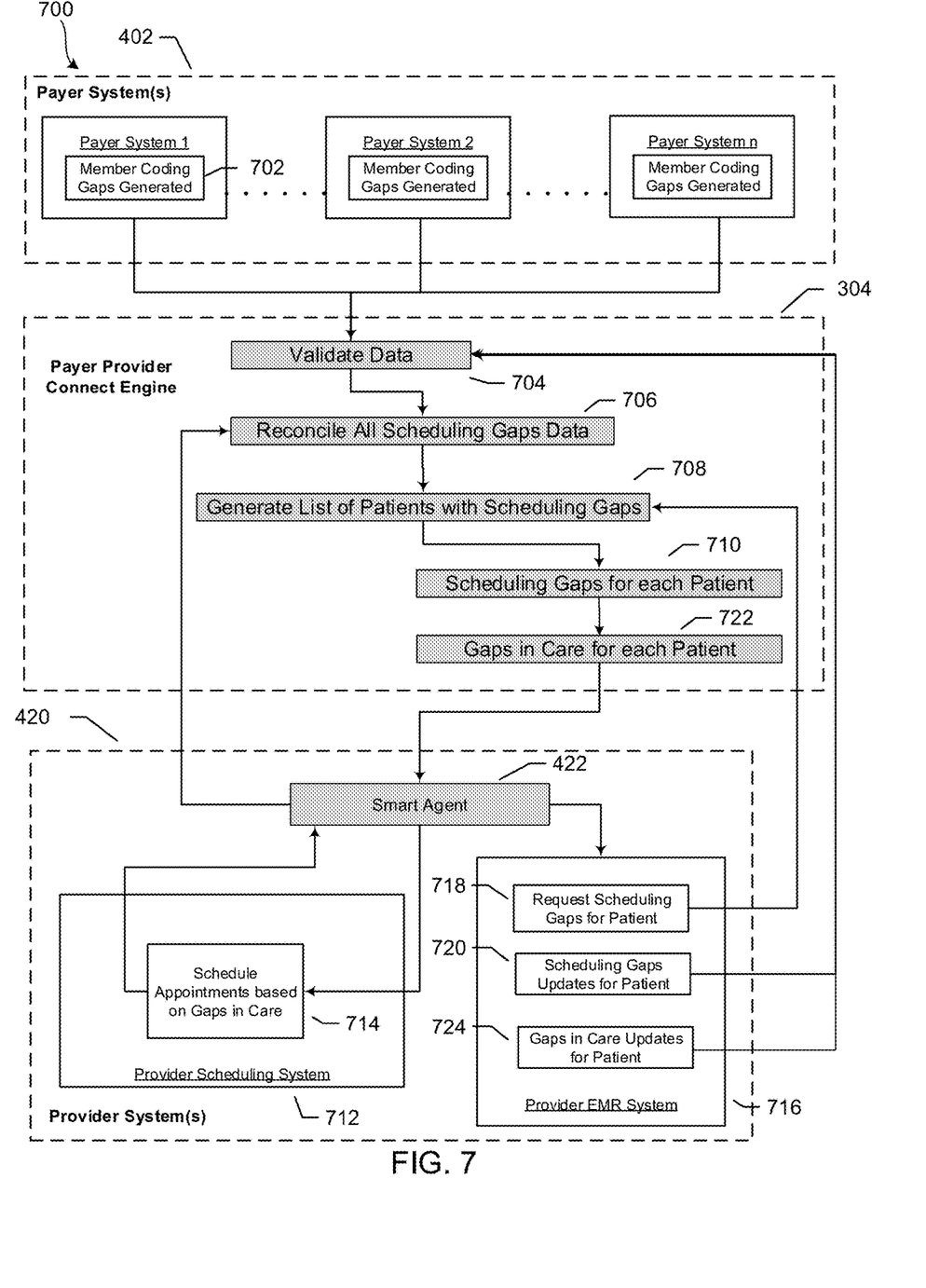
FIG. 7 shows a flow diagram illustrating an example method of operating the system of FIG. 3 for analyzing gaps in care, according to the present disclosure.

Referring now to FIG. 7, in certain aspects, payer system 402 generates member gaps in care 702 and transmits the data to payer provider connect engine 304. Payer provider connect engine 304 validates the data 704, reconciles all gaps in care data 706, generates a list of patients with scheduling gaps 708, and generates the scheduling gaps for each patient 710 as well as gaps in care for each patient 722. The data is sent to smart agent 422. In certain aspects, smart agent 422 unencrypts the file and sends the information to provider scheduling systems 712. Provider scheduling system 712 automatically schedules appointments based on gaps in care 714 and sends to smart agent 422. In certain aspects, smart agent 422 checks for GiC updates and sends the data back to payer provider connect engine 304 to reconcile the new information and send it back out to other provider systems 420. In certain aspects, a scheduler may review the GiC tasks with a patient and completes GiC tasks by scheduling follow-up appointments manually.

In certain aspects, provider EMR system 716 sends a request for scheduling gap update 718 for a given patient to payer provider connect engine 304. In certain aspects, scheduling gaps updates 720 and gaps in care updates 724 are sent to payer provider connect engine 304 Payer provider connect engine 304 reconciles the new information and sends it back out to other provider systems 420.

As mentioned above, the example processes of FIGS. 4, 5, 6, and 7 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 5 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

V. Computing Device

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein may include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and may include volatile and non-volatile, removable and non-removable media for storage of electronic-formatted information such as computer readable program instructions or modules of instructions, data, etc. that may be stand-alone or as part of a computing device. Examples of computer readable storage medium or computer program products may include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein may include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 8:
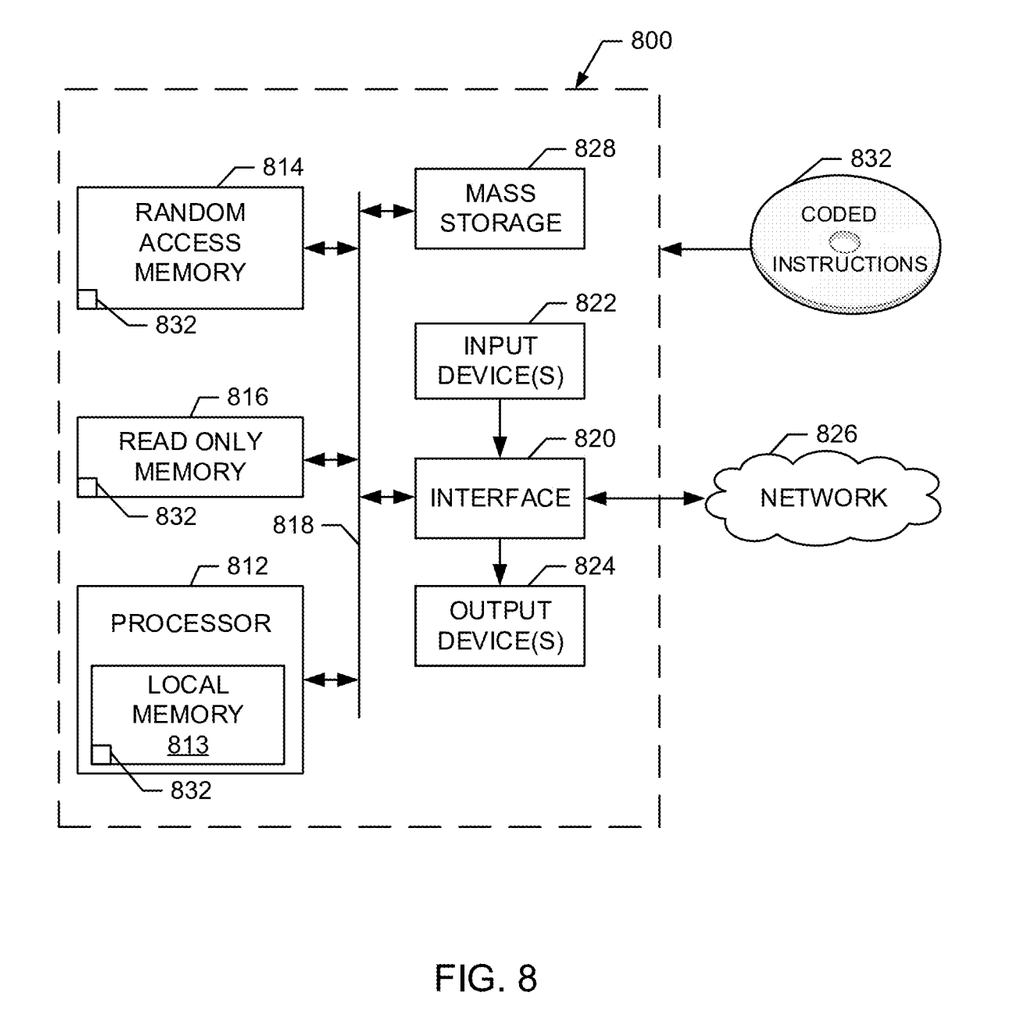
FIG. 8 shows a block diagram of an example processor system that can be used to implement systems and methods described herein.

FIG. 8 is a block diagram of an example processor platform 800 capable of executing the instructions of FIG. 4 to implement the example payer provider connect engine of FIG. 3. The processor platform 800 can be, for example, a server, a personal computer, a mobile device (e.g., a cell phone, a smart phone, a tablet such as an IPAD™), a personal digital assistant (PDA), an Internet appliance, or any other type of computing device.

The processor platform 800 of the illustrated example includes a processor 812. Processor 812 of the illustrated example is hardware. For example, processor 812 can be implemented by one or more integrated circuits, logic circuits, microprocessors or controllers from any desired family or manufacturer.

Processor 812 of the illustrated example includes a local memory 813 (e.g., a cache). Processor 812 of the illustrated example is in communication with a main memory including a volatile memory 814 and a non-volatile memory 816 via a bus 818. Volatile memory 814 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 can be implemented by flash memory and/or any other desired type of memory device. Access to main memory 814, 816 is controlled by a memory controller.

Processor platform 800 of the illustrated example also includes an interface circuit 820. Interface circuit 820 can be implemented by any type of interface standard, such as an Ethernet interface, a universal serial bus (USB), and/or a PCI express interface.

In the illustrated example, one or more input devices 822 are connected to the interface circuit 820. Input device(s) 822 permit(s) a user to enter data and commands into processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to interface circuit 820 of the illustrated example. Output devices 824 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 820 of the illustrated example, thus, typically includes a graphics driver card, a graphics driver chip or a graphics driver processor.

Interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

Processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

Coded instructions 832 of FIG. 4 can be stored in mass storage device 828, in volatile memory 814, in the non-volatile memory 816, and/or on a removable tangible computer readable storage medium such as a CD or DVD.

VI. Conclusion

Thus, certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate improved control over healthcare payer provider connectivity and information flow. For example, certain example systems and methods provide the ability to automatically generate and process gaps in care information from either a healthcare payer and/or healthcare provider. In certain examples, a payer may identify gaps in care based on information in the payer database. The payer can send this information to the provider prior to patient scheduling. The scheduling system at the provider can use this information to schedule patients and their medical needs (e.g., medical test, lab tests, imaging tests, etc.) before the next patient appointment. Primary care providers (PCPs) can then be made aware of the gaps in care information and Hierarchical Condition Category (HCC) coding gaps so they can perform a complete diagnosis using all available clinical data. PCP notes along with the treatment the patient receives can now reflect the required claim diagnosis codes so that the appropriate patient RAF (Risk Adjustment Score) shared by can be computed by the payers. Payer can then be informed electronically that the gap in care has been closed; the payer also can receive claims that allows the RAF score to be computed.

Certain examples leverage information technology infrastructure to standardize and centralize data across an organization. In certain examples, this includes accessing multiple systems from a single location, while allowing greater data consistency across the systems and users.

Technical effects of the subject matter described above may include, but is not limited to, providing system 300 and method 500 which can help generate and process gaps in care using one single unified framework.

Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A payer provider connectivity apparatus, the apparatus comprising:
   a connect engine in communication with a first payer system, a second payer system, and a plurality of provider systems via a network, the connect engine to receive, via the network, medical codes including a first code from the first payer system corresponding to a patient and a second code from the second payer system corresponding to the patient;
   the connect engine including:
      a database to store the medical codes and instructions for execution; and
      a processor to execute the instructions to at least:
         transform the medical codes to a common format, the common format to standardize the first code with the second code to determine a coding gap of the patient, wherein the coding gap is indicative of a gap in care of the patient; and
         when the connect engine determines the coding gap of the patient:
            reconcile the coding gap with a scheduling gap of the patient to schedule an appointment to address the gap in care of the patient, wherein the scheduling gap is indicative of an available time for a provider to remedy the gap in care for the patient; and
   a plurality of smart agents including at least a first smart agent structured to be deployed to a first provider system and a second smart agent structured to be deployed to a second provider system of the plurality of provider systems to enable communication between the first and second provider systems, at least one of the first payer system or the second payer system, and the connect engine, the first smart agent and the second smart agent further structured to process data related to the coding gap when deployed at the respective first provider system and the second provider system, the first smart agent and the second smart agent in communication with the connect engine to:
   reconcile and remove the coding gap from the database corresponding to the patient;
   compute a risk adjustment score with at least one of the first payer system or the second payer system based on a claim diagnosis code triggered by removal of the coding gap; and
   coordinate the appointment scheduled for the patient based on the removal of the gap in care of the patient and the risk adjustment score.

2. The apparatus of claim 1, wherein the gap in care is a gap in a medical care of the patient, wherein the patient is affected negatively by the gap in care.

3. The apparatus of claim 1, wherein the first payer system is to generate a first member roster file and the second payer system is to generate a second member roster file, the first and second member roster files indicative of a plurality of patients associated with the first payer system and the second payer system.

4. The apparatus of claim 3, wherein the connect engine is to receive the first member roster file from the first payer system and the second member roster file from the second payer system, the connect engine further including the processor to:
  transform the first member roster file and the second member roster file to a common format to determine a complete member list of the first payer system and the second payer system;
  reconcile the complete member list with a previous member list to generate a roster exception corresponding to an enrollment status of the plurality of patients; and
  generate instructions to be executed by the respective smart agent at one of the plurality of provider systems to facilitate updating the enrollment status of the plurality of patients.

5. The apparatus of claim 1, wherein the connect engine is to generate a member coding gap file when a first provider system and a second provider system provide a medical code of the patient, the member coding gap file to provide updated information corresponding to a patient medical care to the plurality of provider systems.

6. The apparatus of claim 1, further including a scheduler to receive instructions from the respective smart agent and schedule the appointment based on the gap in care.

7. A method comprising:
  communicating, via a network using a connect engine including a processor, with a first payer system, a second payer system, and a plurality of provider systems, the connect engine to receive, via the network, medical codes including a first code from the first payer system corresponding to a patient and a second code from the second payer system corresponding to the patient;
  storing, in a database using the connect engine, the medical codes and instructions for execution;
  transforming, using the connect engine, the medical codes to a common format, the common format to standardize the first code with the second code to determine a coding gap of the patient, wherein the coding gap is indicative of a gap in care of the patient;
  removing, using at least a first smart agent structured to be deployed to a first provider system and a second smart agent structured to be deployed to a second provider system of the plurality of provider systems to enable communication between the first and second provider systems, at least one of the first payer system or the second payer system, and the connect engine, the coding gap from the database corresponding to the patient, the first smart agent and the second smart agent further structured to process data related to the coding gap when deployed at the respective first provider system and the second provider system;
  computing, using the respective smart agent, a risk adjustment score with at least one of the first payer system or the second payer system based on a claim diagnosis code triggered by removal of the coding gap; and
  coordinating the appointment scheduled for the patient, using the respective smart agent, with the connect engine based on removal of the gap in care of the patient and the risk adjustment score.

8. The method of claim 7, wherein the gap in care is a gap in a medical care of the patient, wherein the patient is affected negatively by the gap in care.

9. The method of claim 7, further including generating a first member roster file and a second member roster file, the first and second member roster file indicative of a plurality of patients associated with the first payer system and the second payer system.

10. The method of claim 9, further including receiving the first member roster file from the first payer system and the second member roster file from the second payer system, and further including:
  transforming the first member roster file and the second member roster file to a common format to determine a complete member list of the first payer system and the second payer system;
  reconciling the complete member list with a previous member list to generate a roster exception corresponding to an enrollment status of the plurality of patients; and
  generating instructions to be executed at one of the plurality of provider systems to facilitate updating the enrollment status of the plurality of patients.

11. The method of claim 7, further including generating a member coding gap file when the first payer system and the second payer system provide a medical code of the patient, the member coding gap file to provide updated information corresponding to a patient medical care to the plurality of provider systems.

12. The method of claim 7, further including receiving instructions and scheduling the appointment based on the gap in care.

13. A non-transitory computer readable storage medium comprising instructions that, when executed, cause at least one processor to at least:
  communicate, via a network using a connect engine, with a first payer system, a second payer system, and a plurality of provider systems, the connect engine to receive, via the network, medical codes including a first code from the first payer system corresponding to a patient and a second code from the second payer system corresponding to the patient;
  store, in a database, the medical codes and instructions for execution;
  transform the medical codes to a common format, the common format to standardize the first code with the second code to determine a coding gap of the patient, wherein the coding gap is indicative of a gap in care of the patient;
  reconcile, when the processor determines the coding gap of the patient, the coding gap with a scheduling gap of the patient to schedule an appointment to address the gap in care of the patient, wherein the scheduling gap is indicative of an available time for a provider to remedy the gap in care for the patient;
  remove, using at least a first smart agent structured to be deployed to a first provider system and a second smart agent structured to be deployed to a second provider system of the plurality of provider systems to enable communication between the first and second provider systems, at least one of the first payer system or the second payer system, and the connect engine, the coding gap from the database corresponding to the patient, the first smart agent and the second smart agent further structured to process data related to the coding gap when deployed at the respective first provider system and the second provider system;

compute, using the respective smart agent, a risk adjustment score with at least one of the first payer system or the second payer system based on a claim diagnosis code triggered by removal of the coding gap; and coordinate the appointment scheduled for the patient, using the respective smart agent, with the connect engine based on removal of the gap in care of the patient and the risk adjustment score.

14. The tangible computer readable storage medium as defined in claim 13, wherein the instructions, when executed, further cause the processer to associate the gap in care with a gap in a medical care of the patient, wherein the patient is affected negatively by the gap in care.

15. The tangible computer readable storage medium as defined in claim 13, wherein the instructions, when executed, further cause the processer to generate a first member roster file and the second payer system is to generate a second member roster file, the first and second member roster file indicative of a plurality of patients associated with the first payer system and the second payer system.

16. The tangible computer readable storage medium as defined in claim 15, wherein the instructions, when executed, further cause the processer to receive the first member roster file from the first payer system and the second member roster file from the second payer system;

transform the first member roster file and the second member roster file to a common format to determine a complete member list of the first payer system and the second payer system;

reconcile the complete member list with a previous member list to generate a roster exception corresponding to an enrollment status of the plurality of patients; and generate instructions to be executed at one of the plurality of provider systems to facilitate updating the enrollment status of the plurality of patients.

17. The tangible computer readable storage medium as defined in claim 13, wherein the instructions, when executed, further cause the processer to generate a member coding gap file when a first provider system and a second provider system provide a medical code of the patient, the member coding gap file to provide updated information corresponding to a patient medical care to the plurality of provider systems.

18. The tangible computer readable storage medium as defined in claim 13, wherein the instructions, when executed, further cause the processer to receive instructions and schedule the appointment based on the gap in care.

* * * * *